(12) United States Patent
LeBlanc et al.

(10) Patent No.: US 7,567,344 B2
(45) Date of Patent: Jul. 28, 2009

(54) APPARATUS AND METHOD FOR CHARACTERIZING DEFECTS IN A TRANSPARENT SUBSTRATE

(75) Inventors: Philip Robert LeBlanc, Corning, NY (US); Vitor Marino Schneider, Painted Post, NY (US); Correy Robert Ustanik, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 11/729,299

(22) Filed: Mar. 28, 2007

(65) Prior Publication Data

US 2007/0263206 A1 Nov. 15, 2007

Related U.S. Application Data

(60) Provisional application No. 60/799,899, filed on May 12, 2006.

(51) Int. Cl.
*G01N 21/00* (2006.01)
(52) U.S. Cl. .............. 356/239.1; 356/237.2; 356/239.8; 430/5; 430/30; 430/311
(58) Field of Classification Search ... 356/237.2–237.6, 356/239.1–239.8
See application file for complete search history.

(56) References Cited

U.S. PATENT DOCUMENTS

| | | | |
|---|---|---|---|
| 3,792,930 A | 2/1974 | Obenreder | 356/209 |
| 5,245,403 A | 9/1993 | Kato et al. | 356/237 |
| 5,333,052 A | 7/1994 | Finarov | 356/369 |
| 5,450,201 A | 9/1995 | Katzir et al. | 356/369 |
| 5,598,262 A | 1/1997 | Jutard et al. | 356/239 |
| 5,831,725 A | 11/1998 | Lee | 356/237 |
| 6,275,286 B1 | 8/2001 | Haubold et al. | 356/239.1 |
| 6,376,829 B1 | 4/2002 | Okugawa | 250/225 |
| 6,437,357 B1 | 8/2002 | Weiss et al. | 250/559.4 |
| 6,618,136 B1 | 9/2003 | Ishida | 356/239.1 |
| 6,806,951 B2 | 10/2004 | Wack et al. | 356/237.2 |
| 6,822,734 B1 | 11/2004 | Eidelman et al. | 356/237.2 |
| 6,829,559 B2 | 12/2004 | Bultman et al. | 702/155 |
| 6,891,610 B2 | 5/2005 | Nikoonahad et al. | 356/237.2 |
| 6,917,419 B2 | 7/2005 | Fielden et al. | 356/237.2 |
| 7,271,889 B2 * | 9/2007 | Cemic et al. | 356/237.2 |
| 2001/0030744 A1 * | 10/2001 | Chang | 356/237.3 |
| 2002/0180985 A1 | 12/2002 | Wack et al. | 356/600 |
| 2003/0025905 A1 | 2/2003 | Meeks | 356/237.3 |
| 2004/0061850 A1 | 4/2004 | Fisch | 356/237.2 |
| 2004/0092045 A1 | 5/2004 | Bultman et al. | 438/16 |
| 2004/0207836 A1 * | 10/2004 | Chhibber et al. | 356/237.4 |
| 2004/0207839 A1 | 10/2004 | Gerstner et al. | 356/239.1 |
| 2005/0146719 A1 | 7/2005 | Chhibber et al. | 356/370 |

(Continued)

FOREIGN PATENT DOCUMENTS

DE    19720308 A1    5/1997

(Continued)

*Primary Examiner*—Gregory J Toatley, Jr.
*Assistant Examiner*—Iyabo S Alli
(74) *Attorney, Agent, or Firm*—Kevin M. Able (57) ABSTRACT

An apparatus and method for detecting defects in a transparent substrate by simultaneously using a combination of bright field and dark field light sources for illuminating the substrate. The apparatus is capable of detecting both inclusions and surface defects simultaneously while the substrate is in motion, simplifying the characterization of substrates in a manufacturing setting.

16 Claims, 5 Drawing Sheets

U.S. PATENT DOCUMENTS

2006/0012780 A1   1/2006   Nishiyama et al. ....... 356/237.4
2006/0244958 A1*  11/2006  Furman et al. ........... 356/237.4

FOREIGN PATENT DOCUMENTS

| | | |
|---|---|---|
| DE | 10057036 A1 | 11/2000 |
| DE | 10102557 A1 | 1/2001 |
| JP | 04168351 | 6/1992 |
| JP | 07234187 | 9/1995 |
| JP | 08327561 | 12/1996 |
| WO | WO2005/073698 A1 | 8/2005 |
| WO | WO2006/029536 A1 | 3/2006 |

* cited by examiner

APPARATUS AND METHOD FOR CHARACTERIZING DEFECTS IN A TRANSPARENT SUBSTRATE

This application claims the benefit of priority under 35 U.S.C. § 119(e) of U.S. Provisional Application Ser. No. 60/799,899 filed on May 12, 2006, the content of which is incorporated herein by reference.

BACKGROUND OF THE INVENTION

1. Field of the Invention

The present invention relates to method for measuring defects in a transparent substrate, and more particularly a method for measuring inclusion and surface defects in the substrate.

2. Technical Background

The growing displacement of cathode ray tubes by flat panels as display devices for computers, televisions, personal digital assistants (PDAs) and cell phones, to name a few, has been nothing short of phenomenal. One principal component to flat panel displays, such as liquid crystal displays (LCDs), is the glass substrate between which the liquid crystal material is sandwiched. Such glass substrates must be pristine in nature, with no visible defects which may be easily discernable by the viewer. Often, multiple display devices are formed on a single substrate, after which the individual displays are cut from the substrate. Thus, glass substrate sheets must be rigorously inspected prior to their use in the manufacture of the display to reduce costs associated with unacceptable substrates.

A traditional inspection system for detecting defects or flaws in a transparent substrate includes an operator who uses one or more light sources to illuminate a substrate at various angles and, based on years of experience, make a determination as to the size and location of defects within the substrate. Often the defects are compared against limit samples to determine whether or not the substrate passes or fails. Defects are then categorized according to the intensity of the light source necessary for detection of the defect. For example, a 20,000 Lux defect is smaller (or fainter) than a 10,000 Lux defect, thereby requiring a higher intensity illumination for detection. Obviously, such a subjective approach to product quality is less than desirable in a modern manufacturing operation.

SUMMARY

In accordance with one embodiment of the present invention, an apparatus for detecting defects in a transparent substrate is described comprising illuminating a portion of the substrate with at least one light source arranged so as to provide dark field illumination of the portion relative to a scanning imaging system, illuminating the substrate portion with at least one light source arranged so as to provide bright field illumination of the portion relative to the scanning imaging system, translating the substrate relative to the scanning imaging system and simultaneously detecting scattered light from the at least one dark field light source and light from the at least one bright field light source by scanning at least a portion of the illuminated portion of the substrate with the scanning imaging system as the substrate is translated.

In another embodiment, an apparatus for detecting defects in a transparent substrate is described comprising at least one bright field light source for illuminating a portion of the substrate at least one dark field light source for illuminating the portion of the substrate, an imaging system for simultaneously receiving light scattered light from the at least one dark field light source and light from the bright field light source and a translating means for translating the substrate relative to the imaging system.

To provide for adjustment of background illumination and image contrast, the light sources are preferably variable. Variability may be automatically controlled by the image processing system in conjunction with the illumination system.

In still another embodiment, an apparatus for detecting defects in a transparent substrate is contemplated comprising a scanning imaging system for scanning the substrate, at least one white light source for illuminating the substrate in the bright field of the imaging system, at least one laser for illuminating the substrate in the dark field of the imaging system, and a translating means for translating the substrate relative to the scanning imaging system while the scanning imaging system is scanning the substrate.

The invention will be understood more easily and other objects, characteristics, details and advantages thereof will become more clearly apparent in the course of the following explanatory description, which is given, without in any way implying a limitation, with reference to the attached Figures. It is intended that all such additional systems, methods, features and advantages be included within this description, be within the scope of the present invention, and be protected by the accompanying claims.

DETAILED DESCRIPTION

In the following detailed description, for purposes of explanation and not limitation, example embodiments disclosing specific details are set forth to provide a thorough understanding of the present invention. However, it will be apparent to one having ordinary skill in the art, having had the benefit of the present disclosure, that the present invention may be practiced in other embodiments that depart from the specific details disclosed herein. Moreover, descriptions of well-known devices, methods and materials may be omitted so as not to obscure the description of the present invention. Finally, wherever applicable, like reference numerals refer to like elements.

Figure 1:
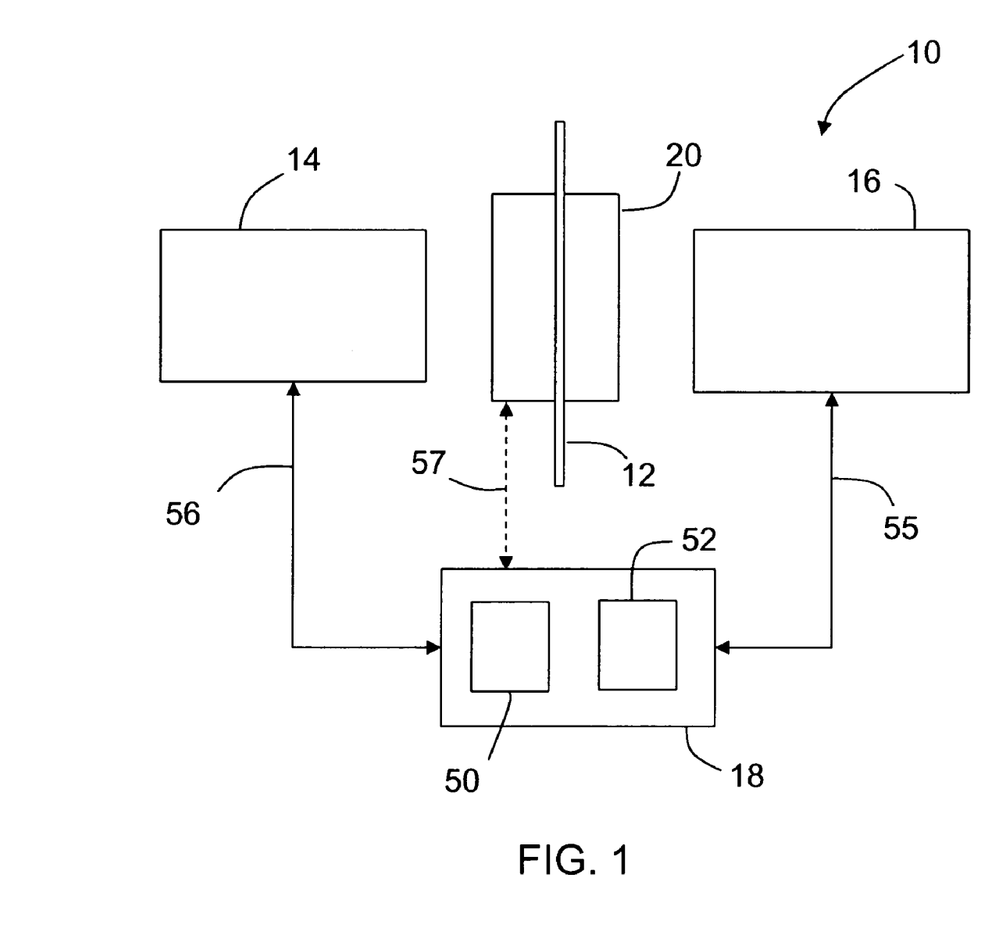
FIG. 1 is a block diagram of an embodiment according to the present invention.

An embodiment of an apparatus 10 for detecting defects in transparent substrate 12 according to the present invention is shown in the block diagram of FIG. 1. Apparatus 10 comprises imaging system 14, illumination system 16, image processing system 18 and transport system 20 for translating substrate 12 relative to imaging system 14 and illumination system 16. Transparent substrate 12 may be glass, plastic, or any other transparent material, and is typically in the form of a sheet having substantially parallel sides (surfaces).

Figure 2:
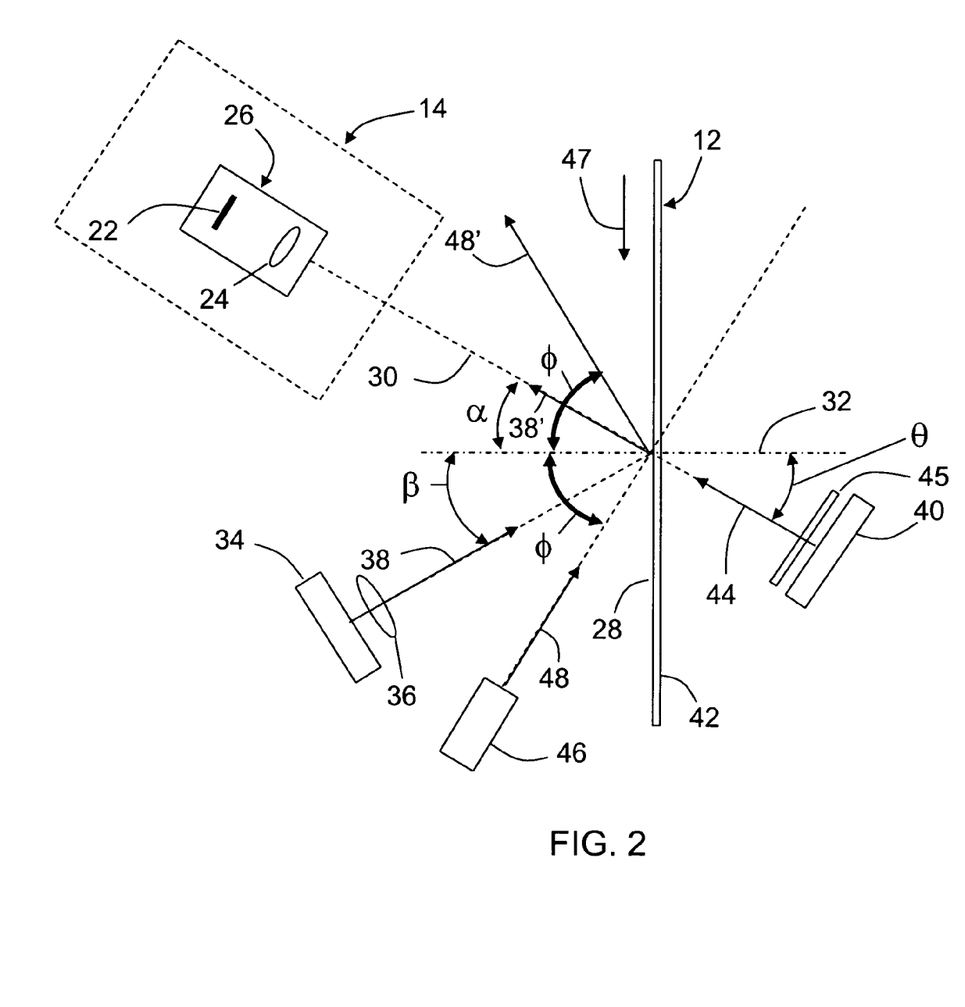
FIG. 2 is a diagrammatic view of an apparatus according to an embodiment of the present invention showing the relative positions of the bright field and dark field light sources with respect to the scanning camera.

As illustrated in FIG. 2, imaging system 14 includes sensor 22 for detecting light impinging on the sensor and converting the light into an electrical signal, and one or more lenses, represented by objective lens 24, for collecting light and directing the light onto sensor 22. For example, sensor 22 and lens 24 may comprise line scanning camera 26. However, imaging system 14 may comprise a point sensor or a sensor which captures a large field of vision as a single image. For purposes of further discussion and not limitation, imaging system 14 will hereinafter be described in terms of a line scanning camera. Line scanning cameras are readily commercially available and may be used to scan narrow swaths of substrate 12 one scan at a time at a rate of several hundred or even thousand scans per second. Sensor 22 may be a CCD sensor, a CMOS sensor or any other sensor type capable of converting light into an electrical signal. Imaging system 14 has a numerical aperture defining the acceptance angle over which the imaging system is capable of receiving light, and is largely controlled by lens 24, and any other aperture-limiting components included with the camera or imaging system, such as an iris.

As shown in FIG. 2, line scanning camera 26 is disposed proximate first surface 28 of substrate 12 such that optical axis 30 of line scanning camera 26 forms an angle α with a normal 32 to first surface 28 (hereinafter surface normal 32). It is assumed that both surfaces of substrate 12 are substantially planar and parallel and that surface normal 32 is a surface normal for both surfaces.

Illumination system 16 serves to illuminate substrate 12 by a variety of methods to identify several species of defect simultaneously. Such defects may be broadly classified as surface defects and interior defects (i.e. inclusions). Surface defects may be, for example, scratches, stains or particulate located on a surface of the substrate. Inclusion defects are such artifacts as bubbles, or metal or silicate particulate fully encased within the interior of the substrate.

For purposes of further discussion, illumination of substrate 12 by illumination system 16 will hereinafter be characterized as bright field illumination or dark field illumination. Bright field illumination occurs when light from a source enters objective lens 24 directly (i.e. enters at an angle which is within the numerical aperture of the imaging system). An image of a defect illuminated in a bright field is formed on sensor 22. Conversely, dark field illumination occurs when light from a source, either transmitted or reflected, and in the absence of scattering from a defect, does not enter objective lens 24. That is, the angle of reflection is such that light reflected from the surface of the glass (either the front surface or the back surface) does not enter objective lens 24. In certain embodiments, illumination system 16 comprises at least one bright field light source and at least on dark field light source.

Referring back to FIG. 2, first light source 34 is disposed such that first light source 34 provides bright field illumination of glass substrate 12 relative to line scanning camera 26. As shown in the embodiment of FIG. 2, first light source 34 is located on the same side of glass substrate 12 as line scanning camera 26 (proximate substrate first surface 28). Light from first light source 34 is focused by lens 36 onto substrate 12 along illumination axis 38. First light source 34 is preferably a polychromatic light source having a wide spectral range, such as a white light source. First light source 34 preferably produces a substantially uniform illumination of at least a portion of substrate 12. When a line scanning camera is used as a detection device, illumination need only be along a narrow swath or strip of substrate 12. The amount of illumination (i.e. surface area) is contingent on the choice of sensor/detection device and the degree of sensitivity of the measurement apparatus to movement (e.g. vibration) of the substrate. At least a portion of the light from light source 34 is reflected from the interior or backside of substrate surface 42 along axis 38', collected by imaging system 14 (e.g. line scanning camera 26) and coupled onto sensor 22, thereby providing bright field illumination of substrate 12 relative to imaging system 14 via a reflection path. However, reflected light which encounters an inclusion is blocked by the inclusion, thereby forming a shadow in the bright field. Although light is also reflected from substrate first surface 28, an effort is made to eliminate as much of the light reflected from substrate surface 28 as possible by appropriate alignment of line scanning camera 26. Ideally, angle β between illumination axis 38 and surface normal 32 is equal to angle α between optical axis 30 and surface normal 32 such that the reflected light is collected by the imaging system and coupled onto sensor 22. However, angle β can be different than angle α as long as illumination angle β is within the acceptance angle of imaging system 14. In one embodiment, angles α and β are each 25° relative to surface normal 32.

Turning again to FIG. 2, second light source 40 is disposed proximate second surface 42 of glass substrate 12, on the side of substrate 12 opposite line scanning camera 26, and provides bright field illumination of the same portion of substrate 12 as is illuminated by first light source 34. Second light source 40 is preferably a polychromatic light source having a wide spectral range, such as a white light source. Second light source 40 can be a fluorescent light source. For example, in order to obtain strip illumination of substrate 12 (illumination along a narrow strip of the substrate), light source 40 may be a straight fluorescent tube. Second light source 40 projects light onto substrate second surface 42 in the direction of illumination axis 44. Ideally, illumination of substrate 12 by second light source 40 is preferably substantially uniform, thereby producing a background illumination of even intensity for that portion of substrate 12 scanned by scanning camera 26 during each scan. However, other intensity patterns may also be acceptable. Diffuser 45 may be placed between second light source 40 and substrate 12 to produce an approximately Lambertian illumination, for example. Fall-off in intensity over the illuminated area of the substrate can be normalized within the imaging system software or camera electronics to produce a substantially uniform field intensity. Ideally, illumination axis 44 coincides with optical axis 30, plus some small displacement due to refraction by the substrate surfaces, of line scanning camera 26 such that angle θ formed between surface normal 32 and illumination axis 44 is equal to angle a between surface normal 32 and line scanning camera optical axis 30. At least a portion of the light projected onto substrate 12 is transmitted through substrate 12 and is collected by line scanning camera 26. Thus, second light source 40 provides bright field illumination of a portion of substrate 12 relative to objective lens 24. It should be noted that angle θ may be different from angle α as long as the angle at which the light from second light source 40 is incident on second surface 42 and transmitted through substrate 12 is within the acceptance angle of line scanning camera 26, e.g. within the camera bright field. Preferably, angle θ should be as small as possible within the foregoing conditions. An angle θ of 15° relative to surface normal 32, for example, has been found to be effective. However, experiments have shown θ may be at least as large as 35° and still provide acceptable results.

It is desirable that the illumination provided by first light source 34 is at least about equal with the amount of illumination provided by second light source 40 (i.e. 1:1). Preferably, the illumination provided by first light source 34 should be greater than the illumination provided by second light source 40. For example, a ratio of intensity between first light source 34 and second light source 40 which has proven to be useful is about 19:1. Of course, the present invention may be used to detect a broad range of defect types, and the intensity ratio between the first and second light sources is a matter of choice. To this end, it is preferable that both first and second light sources 34, 40 be variable so that adjustment may be made to either or both light sources, as needed, to achieve an appropriate contrast level between any substrate defects and the background illumination. The required contrast level is dependent upon, inter alia, the size and type of the defect, ambient light levels (if visual detection is used), sensor sensitivity, imaging software capability, etc.

Third light source 46 is disposed such that light reflected from first and/or second surfaces 28, 42 of substrate 12 does not fall directly on objective lens 24, i.e. in the dark filed of line scanning camera 26. Third light source 46 may be placed anywhere relative to first surface 28 or second surface 42 as long as light from third light source 46 which is reflected from first or second surface 28, 42 is in the dark field of line scanning camera 26 and therefore not directly detected by the camera. Third light source 46 is shown on the same side of glass substrate 12 as line scanning camera 26 (proximate substrate first surface 28) in FIG. 2, and projects light onto substrate 12 along illumination axis 48 at angle φ relative to surface normal 32. At least a portion of the light from third light source 46 in the configuration shown in FIG. 2 is reflected from first surface 28 at angle φ such that the reflected light is within the dark field of line scanning camera 26, i.e. along axis 48'. That is, in the absence of scattering defects, the reflected beam of light does not directly enter objective lens 24 and is not therefore collected by imaging system 14. As with first and second light sources 34, 40, third light source 46 is preferably a light source that can be varied in intensity in order to adjust contrast of the image produced by imaging system 14. In other embodiments, a plurality of dark field light sources may be used as reflecting light sources or transmission light sources. That is, the dark field light sources may be placed on either side of substrate 12.

With dark field illumination, if a scattering defect is present and illuminated by the dark field light source, light is scattered from the defect in a plurality of directions. Some of this light is scattered in the direction of line scanning camera 26 and particularly objective lens 24. If the scattered light is within the acceptance angle of the lens, the scattered light is collected by the lens and directed to sensor 22. To ensure that the scattered light is detectable over the level of background illumination intensity produced by the first and second light sources, it is desirable that the intensity of third light source 46 is significantly greater than the intensity of the first and/or second light sources 34, 40. For example, third light source 46 preferably has an intensity which is at least about an order of magnitude (e.g. at least about 10 times) greater than the intensity of the first or second light sources. While not necessary for operation of the invention, light from a laser is generally capable of providing sufficient intensity to be visible over the bright field illumination. Advantageously, a laser having suitable power, for example, greater than about 10 watts, is capable of producing sufficient scattered optical power to saturate the relevant pixels of sensor 22, producing a bright white indication of the defect against the background illumination produced by the bright field light sources. If a laser is used as third light source 46, it may be desirable to insert a polarizer (not shown) in the optical path between the laser and substrate 12 to prevent a potential increase in background intensity.

As described above, illumination system 16 of the embodiment depicted in FIG. 1 comprises first second and third light sources 34, 40 and 46, respectively.

Images obtained by imaging system 14 may be displayed on a video monitor and monitored by a trained observer to spot defects in the substrate, an approach which is adapted to the use of a broad field of view, single image camera system. A more automated approach may produce superior results, both in terms of consistency and detection level (i.e. the ability to detect extremely small and/or faint defects). In the case of the present embodiment, image processing system 18 is preferably used to collect, store and assemble a plurality of images received from line scanning camera 26. Image processing system 18 preferably comprises a data buffer 50 (memory 50) and processing unit 52 (e.g. computer), for collecting and analyzing data from imaging system 14.

Apparatus 10 further includes a transport system 20 for producing relative motion between transparent substrate 12 and imaging system 14 and illumination system 16. For example, relative motion may be developed by moving substrate 12 relative to imaging system 14 and illumination system 16, as indicated by arrow 47. Alternatively, relative motion may be developed by moving imaging system 14 and/or illumination system 16 relative to substrate 12. As glass substrates for use in display applications grow in size, moving the optics and illumination sources may become an attractive alternative to moving the glass substrate. However, alignment of the optics is easier if the optical elements do not move. Transport system 20 may comprise, for example, a linear stage, stepper motors, conveyor belts, tracks, carriages, pneumatic tables (air bearings), or other conventional methods of conveying either a substrate, camera and/or light sources. For purposes of discussion and not limitation, it will be hereinafter assumed that the substrate is moved relative to the imaging and illumination systems. Transport system 20 preferably is also capable of moving the substrate and/or imaging system in a direction of surface normal 32 to maintain a consistent distance between substrate 12 and imaging system 14. Further, transport system 20 may also perform a flattening function to maintain the illuminated portion of the substrate flat during scanning. Flattening may be performed in a conventional manner. For example, air pressure (e.g. air bearings), may be used to flatten a portion of the substrate.

The operation of apparatus 10 may proceed in the following manner. As substrate 12 is moved past imaging system 14, light from first light source 34 falls on substrate 12 along axis 38 and a portion of the light is reflected from substrate second surface 42 along axis 38' to line scanning camera 26. Simultaneously with the first light source, light from second light source 40 falls on substrate 12 along illumination axis 44 at angle θ relative to surface normal 32. At least a portion of the light incident on substrate 12 from source 40 is transmitted through the substrate and is collected by line scanning camera 26. The combination of transmitted light from second light source 40 and reflected light from first light source 34 makes possible detection of inclusions within the body of the substrate, including bubbles (seeds), and solid particulate.

Additionally, light from third light source 46 falls on substrate 12 along illumination axis 48 at an angle φ that ensures that the light reflected from substrate first surface 28 along axis 48' is not captured by imaging system 14. (Light from third light source 46 is transmitted through the substrate and also falls on and is reflected from second surface 42.) Scattering defects illuminated by light source 46 scatter the light striking the defect, a portion of the scattered light falling within the acceptance angle of imaging system 14. Because defect detection using a dark field light source is relying on only a small portion of the light from the light source which is incident on and scattered by the defect, third light source 46 is preferably a laser, or at least a source having a high luminance compared to first and second light sources 34, 40. Thus, light from third light source 46 which is scattered by the defect and captured by the imaging system has a significantly higher intensity that the reflected and transmitted light from the first and second light sources and is therefore clearly visible to the imaging system, even against the bright field of the first and second light sources.

Figure 3:
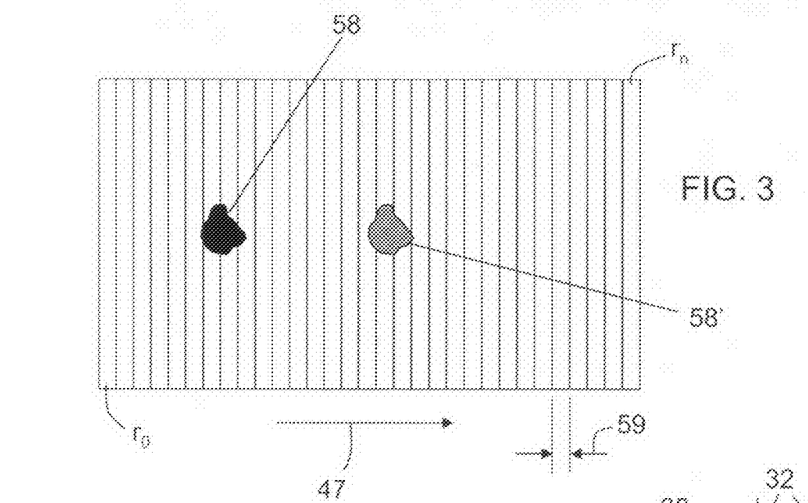
FIG. 3 is an illustration of substrate to be measured showing a plurality of scans performed by a line scanning camera, and the primary and secondary images of an inclusion.

As depicted in FIG. 3, line scanning camera 26 makes repetitive scans of substrate 12, where $r_0$ represents a scan at time zero (first scan) and $r_n$ represents the scan at time n (e.g. the last scan). However, since substrate 12 is moving relative to the field of view of line scanning camera 26 (indicated by arrow 47), the camera captures scans of successive swaths or strips of substrate 12 as illustrated in FIG. 3. As described previously, line scanning camera 26 may make a thousand or more scans per second of substrate 12, wherein a single scan of substrate 12 may cover a width of less than about 20 μm. For example, it is not unusual according to the present invention for line scanning camera 26 to make in excess of 200,000 scans in order to cover a small portion of the substrate to be measured. Data for each scan is transferred to image processing system 18 via data line 56 and stored in buffer 50 (memory). Processing unit 52 uses the stored data to assemble an image of a portion of substrate 12, and perform characterizing calculations necessary to identify and categorize substrate defects.

If desired, the background illumination may be normalized by image processing system 18. For example, in an 8-bit imaging system, the dynamic range of the system is represented by 256 grey scale values ranging from the lightest value 255 (e.g. white) to the darkest value 0 (black). The background data may be normalized such that the background illumination is represented by a grey value of about 128±δ, where δ represents a pre-determined threshold value. Accordingly, grey values above or below 128±δ may be treated as defects. The value of δ is dependent upon the pass/fail criteria applied and is user dependent.

Image processing system 18 may be used to automatically control illumination system 16, such as illumination intensities, through data line 55, and to also control transport system 20, such as by controlling the rate of movement of substrate 12 (or imaging system 14) through data line 57.

Figure 4:
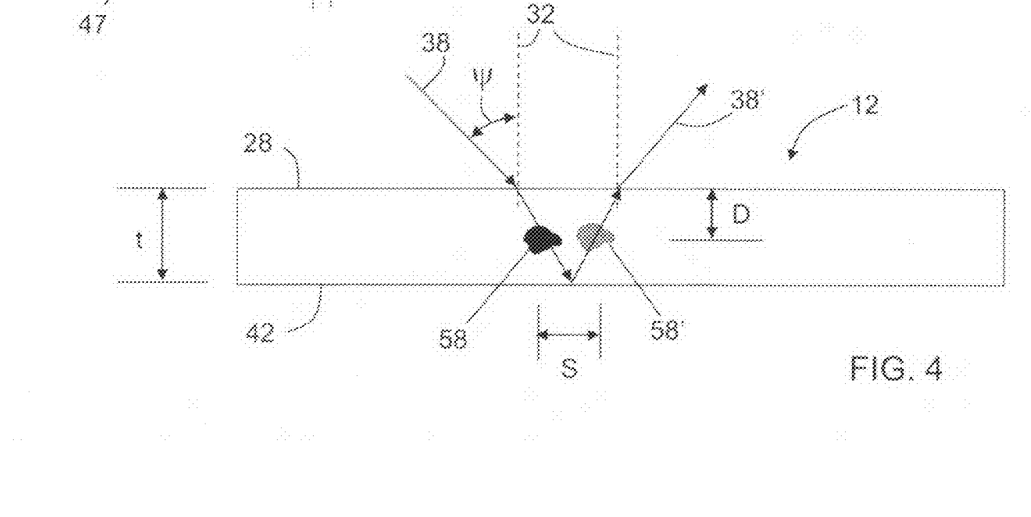
FIG. 4 is an edge cross sectional view of the substrate of FIG. 3 showing the basis for a principal and secondary image of an inclusion, and the parameters for determining an approximate depth for an inclusion.

An example of the scanning of a portion of a substrate is shown in FIG. 4, wherein each scan used to assemble an image of the substrate is represented from $r_0$ to $r_n$, and each scan has a width represented by the distance 59. As shown, both a first image and a second, ghost image, of a defect appears within the generated substrate image. In accordance with FIG. 4, light from first light source 34 is incident on substrate first surface 28, is refracted and initially blocked by inclusion 58. The light from first light source 34 that is blocked by inclusion 58 is represented by the primary dark image in FIGS. 3 and 4. As substrate 12 moves to the right in the illustration (e.g. arrow 47), inclusion 58 moves into a new position relative to imaging system 14 where light from first light source 34 which is now reflected from the backside (interior) of second surface 42 is blocked by the new location of the inclusion. Thus, a ghost, or secondary, image of the inclusion is shown (represented by the gray image 58' in FIGS. 3 and 4).

Advantageously, an approximate depth of an inclusion may also be calculated. The approximate depth may be used, for example, to estimate the proximity of the defect to the surface of the substrate, which may be used indirectly to infer, for example, the likelihood that the inclusion results in a surface defect based on the proximity of the inclusion to the substrate surface.

Referring again to FIG. 4, an approximate depth of inclusion 58 may be determined in accordance with the following simple formula:

$$D=t-(s/2)\tan(\sin^{-1}(\sin(\psi)/n)) \quad (1)$$

Wherein D is the approximate depth of the inclusion, t is the thickness of the substrate, s is the distance between the primary inclusion image and the secondary (ghost) inclusion image, ψ is the angle between the incident light and a normal 32 to the substrate surface, and n is the refractive index of the substrate. A size may also be estimated for the inclusion if desired, and may be calculated by known methods based on the measured intensities.

In a simpler implementation of the prior embodiment (not shown), a single bright field light source may be used, along with a single dark field light source. For example, either first light source 34 may be removed (or turned off), or second light source 40 may be removed (or turned off). The principals of the single bright field, single dark field embodiment are the same as previously discussed. Preferably, the dark field light source is a laser. Preferably the intensity of the laser is at least about 10× greater than the intensity of the bright field light source.

Figure 5:
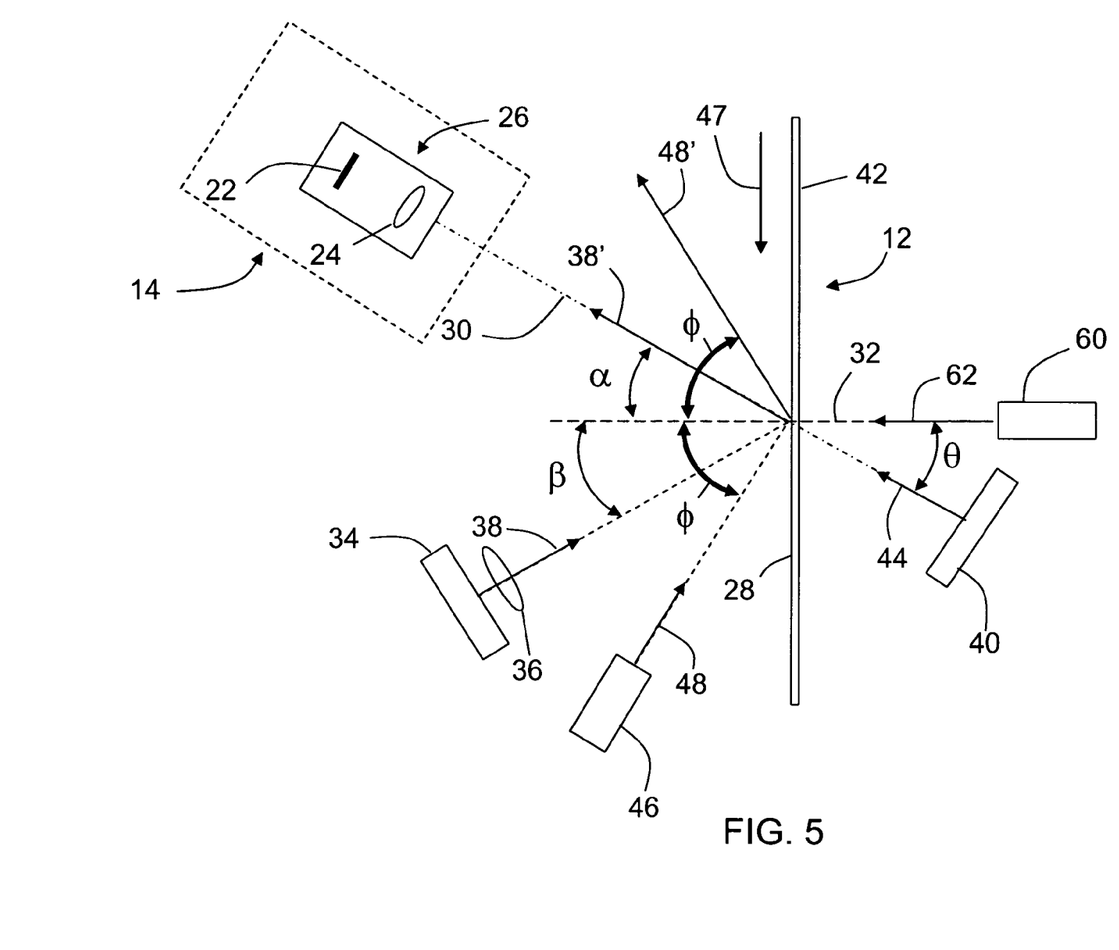
FIG. 5 is a diagrammatic view of an apparatus according to another embodiment of the present invention showing the relative positions of the bright field and dark field light sources with respect to the scanning camera.

In another embodiment, illumination system 16 may comprise multiple dark field light sources. Illustrated in FIG. 5 is an exemplary configuration depicting two dark field light sources, third light source 46 as in the previous embodiment, and an additional fourth light source 60. As in the previous embodiment, dark field light sources 46, 60 have an intensity which is substantially greater than the intensity of bright field light sources 34, 40. In the embodiment shown in FIG. 5, dark field light source 46 is on the same side of substrate 12 as line scanning camera 26 (proximate substrate surface 28), and the second dark field light source 60 is on the same side of substrate 12 as second (bright field) light source 40. Preferably, dark field light sources 46, 60 are lasers. As illustrated in FIG. 5, fourth light source 60 has an illumination axis 62 which is preferably coincident with surface normal 32. It should be noted that third and fourth light sources 46, 60 may be placed at any angle with respect to surface normal 32 as long as light from the sources which is reflected from the substrate (in the absence of scattering), or transmitted through the substrate, is not collected in the bright field of the imaging system. That is, the dark field character of the light sources as previously defined is preserved. Generally, it has been found that angles which place the illumination angle of the dark field light sources closer to the surface normal are less sensitive to positional error than illumination axes which have more glancing angles.

As previously described, transport system 20 produces relative motion between substrate 12 and imaging system 14.

Figure 6:
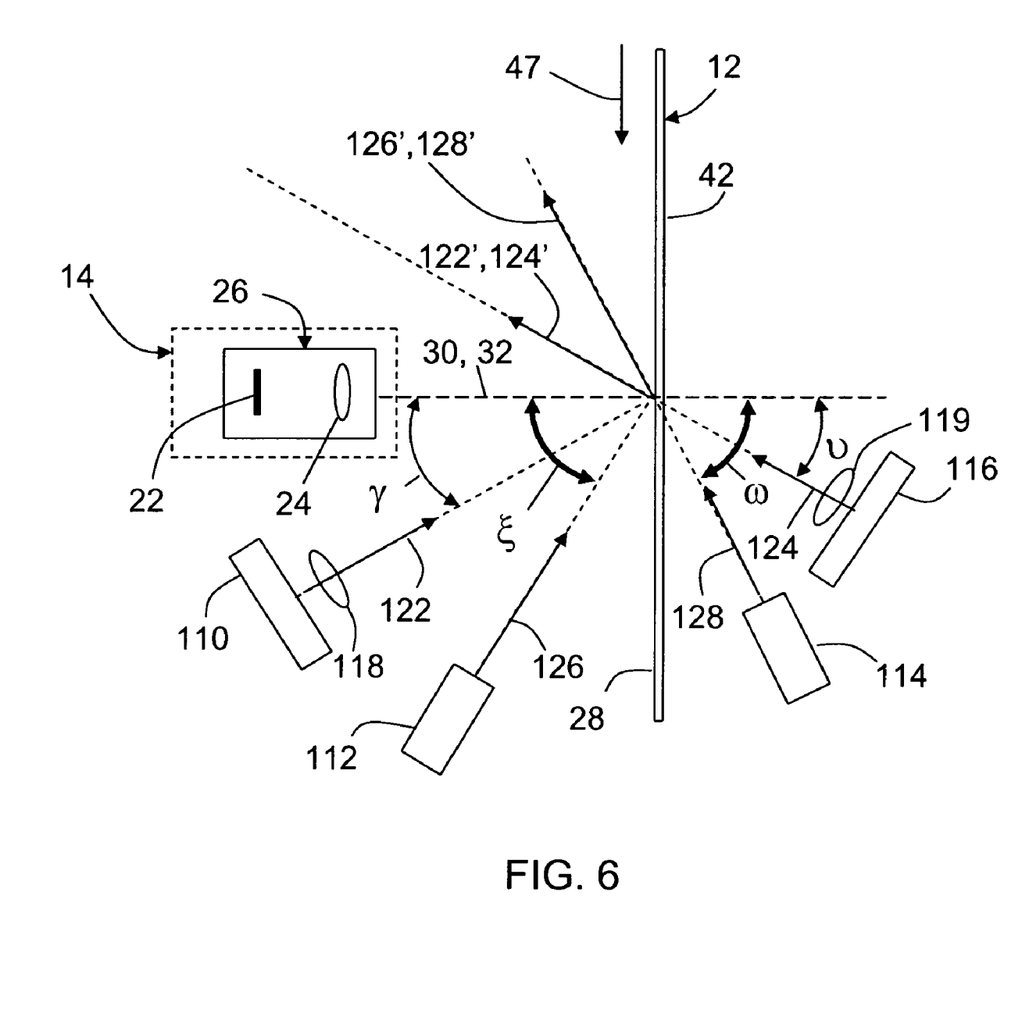
FIG. 6 is a diagrammatic view of an apparatus according to still another embodiment of the present invention showing the relative positions of the dark field light sources with respect to the scanning camera.

In still another embodiment, illumination system 16 employs dark field illumination only. An exemplary illustration of a dark field-only system is shown in FIG. 6. As depicted in FIG. 6, line scanning camera 26 is placed proximate substrate first side 28. In the illustrated embodiment, optical axis 30 is coincident with surface normal 32. Illumination system 16 comprises four light sources, 110, 112, 114 and 116. First and second light sources 110, 112 are disposed on the same side of substrate 12 as line camera 26 and operate as reflecting dark field light sources relative to imaging system 14 (i.e. line scanning camera 26). Third and fourth light sources 114, 116 are disposed proximate substrate second side 42 and operate as transmission dark field light sources relative to line scanning camera 26.

First and fourth dark field light sources 110, 116 are preferably polychromatic light sources having a broad spectral width (e.g. white light sources), and are both focused onto substrate 12 by lenses 118, 119 respectively. However, one or both of first and fourth dark field light sources may be diffused light rather than focused light. For example, one white light source may be focused and the other diffused. First and fourth dark field light sources 110, 116 are preferably variable in intensity to allow for contrast adjustment.

Second and third dark field light sources 112, 114 are preferably lasers and are also preferably variable in intensity. Of course, care should be taken to ensure that sensor 22 is suitably sensitive at the wavelength of the laser(s). Polarizers (not shown) may be used in front of second and third light sources 112, 114 if desired or needed to reduce background illumination.

As shown in FIG. 6, first and fourth dark field light sources 110, 116 are positioned within close proximity to optical axis 30. First dark field light source 110 illuminates substrate 12 with light along illumination axis 122 at angle $\gamma$ relative to surface normal 32. Light from first light source 110 which is reflected from second surface 42 is reflected from the surface at the same angle $\gamma$ along axis 122', although displaced slightly due to refraction at surface 28.

Light from fourth dark field light source 116 illuminates substrate 12 along illumination axis 124 at angle $\nu$ relative to surface normal 32. At least a portion of the light from fourth light source 116 is transmitted through substrate 12 along axis 124'. Light from fourth dark field light source is focused on substrate 12 by lens 119.

Substrate 12 is further illuminated by second dark field light source 112 along illumination axis 126 at angle $\xi$ relative to surface normal 32. At least a portion of the light from second light source 112 is reflected from first surface 28 along axis 126', also at angle $\xi$ relative to surface normal 32. The reflected light (in the absence of scattering), is not collected by line scanning camera 26.

Finally, substrate 12 is illuminated by third dark field light source 114 along illumination axis 128 at angle $\omega$ relative to surface normal 32. At least a portion of the light from third light source 114 is transmitted through substrate 12 along axis 128'.

In the illustrate embodiment, angles $\gamma$ and $\nu$ are equal and angles $\xi$ and $\omega$ are equal. However, angles $\gamma$ and $\nu$ need not be equal, nor do $\xi$ and $\omega$ need be equal. Moreover, although FIG. 6 depicts four dark field light sources, more or fewer dark field light sources may be used. For example, two dark field light sources, one illuminating each surface of substrate 12 may be used. Alternatively, additional dark field light sources may be added to the configuration illustrated in FIG. 6. In one embodiment a diffuser may be used between second dark field light source 112 and substrate 12. A suitable line diffuser, for example, can be model FOLM-23 manufactured by OZ Optics.

As in the embodiments disclosed supra, transport system 20 may be used to translate substrate 12 relative to imaging system 14 while scanning camera 26 scans the substrate along narrow strips of the substrate and the individual images are stored in data buffer 50. Image processing system 18 assembles the individual images into a single image of the substrate, and characterizes the substrate with respect to the presence of defects as previously described.

As in the case of the previous embodiments, if a line scanning camera is used in the imaging system, only a narrow swath or strip of the substrate need be illuminated at any given time. Thus, appropriate adaptation of the light sources to produce only narrow illumination of substrate 12 may be employed. For example, the broadband (white) light sources may be fluorescent tubes, or incandescent lights which are channeled into a linear array by fiber optics. Suitable devices for accomplishing this task are readily commercially available.

It should be emphasized that the above-described embodiments of the present invention, particularly any "preferred" embodiments, are merely possible examples of implementations, merely set forth for a clear understanding of the principles of the invention. Many variations and modifications may be made to the above-described embodiments of the invention without departing substantially from the spirit and principles of the invention. For example, for large size substrates, such as glass display substrates, multiple apparatuses in accordance with the present invention may be combined to ensure characterization of a substantial portion of the substrate is performed. For example, several apparatuses may be placed end to end, or staggered, in a production line to scan the entire substrate. All such modifications and variations are intended to be included herein within the scope of this disclosure and the present invention and protected by the following claims.

What is claimed is:

1. A method for detecting defects in a transparent substrate comprising:
   providing a transparent substrate comprising a front surface and a back surface;
   illuminating an interior portion of the transparent substrate with at least one light source arranged to provide dark field illumination of the interior portion relative to a scanning imaging system;
   illuminating the transparent substrate interior portion with at least one light source arranged to provide bright field illumination of the interior portion relative to the scanning imaging system, wherein light comprising the bright field illumination enters the interior portion through the transparent substrate front surface and is reflected from the transparent substrate back surface within the interior portion of the transparent substrate;
   translating the transparent substrate relative to the scanning imaging system; and
   simultaneously detecting the light from the at least one bright field light source reflected from the back surface of the transparent substrate and light scattered by a defect within the interior portion illuminated by the dark field illumination by scanning the transparent substrate with the scanning imaging system while the transparent substrate is translated.

2. The method according to claim 1 further comprising illuminating the interior portion of the substrate with a plurality of dark field light sources.

3. The method according to claim 1 further comprising illuminating the interior portion of the transparent substrate with a plurality of bright field light sources.

4. The method according to claim 1 wherein the bright field light source is a white light source.

5. The method according to claim 1 wherein the dark field light source is a laser.

6. The method according to claim 1 further comprising diffusing the light from the bright field light source prior to illuminating the interior portion of the transparent substrate with the bright field light source.

7. The method according to claim 1 wherein an optical intensity of the at least one bright field light source and the at least one dark field light source is variable.

8. The method according to claim 1 wherein the scanned interior portion during a single scan is less than about 20 μm wide.

9. The method according to claim 2 wherein both the front surface and the back surface are illuminated by the plurality of bright field light sources.

10. The method according to claim 3 wherein both the front surface and the back surface are illuminated by the plurality of bright field light sources.

11. An apparatus for detecting defects in a transparent substrate comprising:
a first bright field light source arranged to direct a first bright field light through a back surface of the transparent substrate;
a second bright field light source arranged to direct a second bright field light through a front surface of the transparent substrate;
a first dark field light source arranged to directing a dark field light though the front surface of the transparent substrate;
a scanning imaging camera arranged opposite the front side surface of the transparent substrate for simultaneously receiving the first and second bright field lights, and dark field light from the first dark field light source scattered by a defect in an interior of the transparent substrate; and
a translating means for translating the substrate relative to the imaging system.

12. The apparatus according to claim 11 further comprising a plurality of dark field light sources.

13. The apparatus according to claim 11 wherein the first and second bright field light sources are white light sources.

14. The apparatus according to claim 13 wherein the first dark field light source is a laser.

15. An apparatus for detecting defects in a transparent substrate comprising:
first and second white light sources for illuminating an interior portion of the transparent substrate in the bright field of the imaging system, the first and second light sources arranged opposite front and back surfaces of the transparent substrate, respectively;
first and second dark field light sources arranged opposite the front and back surfaces of the transparent substrate, respectively;
a line scanning camera arranged opposite one of the front or back surfaces for scanning the transparent substrate;
a translating means for translating the transparent substrate relative to the scanning imaging camera while the scanning imaging system is scanning the transparent substrate; and
wherein the line scanning camera simultaneously detects light from the first and second bright field light sources and the first and second dark field light sources to detect defects on a surface and within an interior of the transparent substrate.

16. The apparatus according to claim 11 further comprising a second dark field light source arranged to direct a dark field light through the back surface of the transparent substrate.

* * * * *

UNITED STATES PATENT AND TRADEMARK OFFICE
CERTIFICATE OF CORRECTION

PATENT NO. : 7,567,344 B2  Page 1 of 1
APPLICATION NO. : 11/729299
DATED : July 28, 2009
INVENTOR(S) : Philip Robert LeBlanc et al.

It is certified that error appears in the above-identified patent and that said Letters Patent is hereby corrected as shown below:

| No. | Col. | Line | Description |
|---|---|---|---|
| 1 | 11 | 27 | Please delete "though" and add "through" |

Signed and Sealed this

Seventeenth Day of November, 2009

David J. Kappos
*Director of the United States Patent and Trademark Office*